United States Patent [19]

Mainz

[11] Patent Number: 5,344,486
[45] Date of Patent: Sep. 6, 1994

[54] PLATELET-LIKE PIGMENTS

[75] Inventor: Bernhard Mainz, Darmstadt, Fed. Rep. of Germany

[73] Assignee: Merck Patent Gesellschaft mit beschrankter Haftung, Darmstadt, Fed. Rep. of Germany

[21] Appl. No.: 13,840

[22] Filed: Feb. 5, 1993

[30] Foreign Application Priority Data

Feb. 7, 1992 [DE] Fed. Rep. of Germany ....... 4203501

[51] Int. Cl.5 ..................... C09C 1/34; B32B 33/00; B32B 19/00
[52] U.S. Cl. .................................. 106/415; 106/437; 106/439; 106/450; 106/453; 106/459; 106/499; 428/404
[58] Field of Search ................ 106/415, 418, 437–499; 428/403, 404; 423/290

[56] References Cited

U.S. PATENT DOCUMENTS 3,144,305  8/1964  O'Connor ............................ 423/290

FOREIGN PATENT DOCUMENTS 3922178   1/1971   Fed. Rep. of Germany .
61-100508 5/1986   Japan ............................ A61K 7/00
62-187405 8/1987   Japan ............................ A61K 7/00
277281   11/1988   Japan .
1320513   6/1973   United Kingdom .

Primary Examiner—Paul Lieberman
Assistant Examiner—Margaret Einsmann
Attorney, Agent, or Firm—Millen, White, Zelano & Branigan

[57] ABSTRACT

The invention relates to pigments based on platelet-like substrates substantially composed of nitridic material and coated with at least one dye and/or one metal oxide, and to processes for their preparation and also to their use in cosmetic preparations.

13 Claims, No Drawings

PLATELET-LIKE PIGMENTS

BACKGROUND OF THE INVENTION

The invention relates to platelet-like pigments, in particular for cosmetic applications. Platelet-like pigments, i.e., platelet-shaped materials of relatively low thickness relative to their length and width, such as, for example, mica platelets coated with metal oxides or dyes, are used not only for the pigmenting of varnishes, inks, plastics and the like but also in cosmetic preparations. For some applications, the strong pearly luster of such preparations is undesirable. A further disadvantage, in particular for cosmetic applications, is that preparations containing such pigments do not have desirable soft tactile properties. These properties can be improved with further additives. For example, the addition of spherical particles, as described in DE 3,922,178, is suitable for this purpose. However, there still remains the object of providing, in particular for cosmetic applications, pigments having a matte satin-like luster and pleasantly soft tactile properties. Surprisingly, it has been found that platelet-like nitridic materials are highly suitable for the preparation of layer/substrate pigments.

SUMMARY OF THE INVENTION

Accordingly, an object according to the invention is achieved by providing novel pigments composed of nitridic material and coated with at least one dye and/or metal oxide. The invention therefore relates to platelet-like pigments composed of nitridic material coated with at least one dye and/or metal oxide.

The pigments according to the invention contain a metal nitride, such as, for example, aluminum nitride or boron nitride, as support. Of these, boron nitride (BN) is preferred as the support material. Preference is given to platelet-like BN. This BN is prepared by known processes. Details on suitable preparation processes can be found in handbooks, for example Ullmann's Encyclopedia of Industrial Chemistry, Volume A 4, 5th edition (1985); Verlag Chemie, and in the patent literature, for example DE 1,943,582. Preference is given to particles having the following dimensions: thickness 0.02–0.5 $\mu$m; diameter 8–40 $\mu$m; particular preference is given to particles having the dimensions thickness 0.08–0.13 $\mu$m and diameter 15–25 $\mu$m.

Dyes and metal oxides suitable for coating and their precursors are known to one skilled in the art. The following list of proven dyes is solely intended to illustrate the invention without limiting it in any way. Compounds of this type include, for example, inorganic dyes, such as, for example, Prussian blue, organic dyes, such as, for example, carmine or 1,4-diketopyrrolo-(3,4-c-pyrrole (DPP red), colored or uncolored metal oxides or mixed oxides, such as for example, $Fe_2O_3$, $Fe_3O_4$, $Al_2O_3$, $ZrO_2$, $Cr_2O_3$, $Fe_2TiO_5$ and $TiO_2$. The dyes and/or metal oxides are usually used in relative amounts of 1–70%, preferably 5–60%, these numbers referring to the weight ratios of amount of metal oxide applied versus coated pigment.

Furthermore, the invention relates to processes for the preparation of platelet-like pigments coated with at least one dye and/or metal oxide. All processes known per se for the coating of substrates can be used for this. Details of such processes are known to one skilled in the art, inter alia, from the patent literature. Examples of such processes and references to the patent literature are:

a) The dye or metal oxide is applied to the nitridic material from a solution or a fine dispersion additionally containing the nitridic material as suspension; cf. EP 0,339,399 (corresponding to U.S. Pat. No. 5,118,352) or U.S. Pat. No. 4,772,331.

b) The precursor of a dye is converted into the dye in a solution additionally containing the nitridic material as suspension, and the dye formed is applied to the nitridic material; cf. DE 3,536,168 (corresponding to U.S. Pat. No. 4,806,128).

c) A precursor of a dye applied to a nitridic material is converted into a dye; cf. DE 2,313,332 (corresponding to U.S. Pat. No. 3,951,679) or DE 2,429,762 (corresponding to U.S. Pat. No. 4,084,983).

d) A precursor of a metal oxide is converted into the metal oxide in a solution additionally containing the nitridic material as suspension, and the metal oxide formed is applied to the nitridic material; cf. DE 3,154,354 or DE 3,154,355 (corresponding to U.S. Pat. Nos. 4,494,993 and 4,509,988, respectively).

e) A precursor of a metal oxide applied to a nitridic material is converted into a metal oxide; cf. DE 2,244,298 (corresponding to U.S. Pat. No. 3,874,890).

The patent literature mentioned furthermore contains references describing further processes known to one skilled in the art.

The invention furthermore relates to cosmetic preparations containing platelet-like pigments composed of a nitridic material coated with at least one dye and/or metal oxide. Suitable compositions for cosmetic preparations of this type, such as, for example, powders or creams, are known to one skilled in the art.

The invention furthermore relates to the use of platelet-like pigments composed of a nitridic material coated with at least one dye and/or metal oxide in the production of cosmetic preparations. Processes for the production of cosmetic preparations, such as, for example, powders or creams, are known to one skilled in the art.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

The entire disclosure of all applications, patents and publications, cited above and below, and of corresponding German No. P 42 03 501.5, are hereby incorporated by reference.

EXAMPLES

EXAMPLE 1: Coating of boron nitride with Prussian blue

In a stirred reactor, the following two aqueous solutions (500 ml each):

a) $FeCl_3$ solution (containing 10 g/l of Fe; adjusted to a pH of 3–)

b) $K_4[Fe(CN)_6] \times 3$ $H_2O$ solution (59 g/l) are added simultaneously to a suspension of 50 g of BN (particle size: diameter 20 $\mu$m, thickness 0.1 $\mu$m) in 2 l of $H_2O$ adjusted to a pH of 4.0 at 75° C. over a period of 3 hours with stirring (1000 rpm). Stirring is then continued for 15 minutes. The reaction product is filtered off with suction, washed and dried at 120° C.

The product is a blue pigment having a silky matte luster and pleasant tactile properties.

EXAMPLE 2: Coating of boron nitride with $TiO_2$

In a stirred reactor, 300 ml of an aqueous solution of $TiCl_4$ (300 g/l) are added to a suspension of 50 g of BN (particle size: diameter 20 μm, thickness 0.1 μm) in 2 l of $H_2O$ adjusted to a pH of 2.2 at 75° C. over a period of 3 hours with stirring (800 rpm).

The reaction product is filtered off with suction, washed, dried and then calcined at 800° C. for 30 minutes. This gives a white pigment having a titanium dioxide content of 43% and pleasant tactile properties.

EXAMPLE 3: coating of boron nitride with $TiO_2$

In a stirred reactor, 400 ml of an aqueous solution of $TiCl_4$ (360 g/l) are added to a suspension of 50 g of BN (particle size: diameter 20 μm, thickness 0.1 μm) in 1 l of $H_2O$ adjusted to a pH of 2.2 at 75° C. over a period of 3 hours with stirring (1000 rpm).

The reaction product is filtered off with suction, washed, dried and then calcined at 800° C. for 30 minutes and screened (mesh size 65 μm). It has a titanium dioxide content of 54%.

EXAMPLE 4: Coating of boron nitride with $Fe_2O_3$

In a stirred reactor, 500 ml of an aqueous solution of $FeCl_3$ (19 g of Fe/l) are added to a suspension of 50 g of BN (particle size: diameter 20 μm, thickness 0.1 μm) in 2 l of $H_2O$ adjusted to a pH of 4.0 at 75° C. over a period of 4 hours with stirring (1000 rpm).

The reaction product is filtered off with suction, washed with 8 l of $H_2O$, screened (mesh size 100 μm), dried, then calcined at 800° C. for 30 minutes and screened again (mesh size 63 μm). It has an $Fe_2O_3$ content of 21%.

EXAMPLE 5: Coating of boron nitride with $Fe_2TiO_5$

In a stirred reactor, the following two aqueous solutions:

a: 93 ml of $FeCl_3$ solution (containing 150 g/l of Fe; adjusted to a pH of 3–4)

b) 64.5 ml of $TiCl_4$ solution (370 g/l)

are added simultaneously to a suspension of 50 g of BN (particle size: diameter 20 μm, thickness 0.1 μm) in 2 l of $H_2O$ adjusted to a pH of 2.6 at 75° C. over a period of 3 hours with stirring (1000 rpm).

The reaction product is filtered off with suction, washed with 8 l of $H_2O$, dried at 120° C., screened (mesh size 100 μm), then calcined at 800° C. for 30 minutes and screened again (mesh size 63 μm). Its metal oxide content is 37%.

EXAMPLE 6: Coating of boron nitride with titanium compounds and iron compounds In a stirred reactor, 64.5 ml of aqueous $TiCl_4$ solution (370 g/l) are added to a suspension of 50 g of BN (particle size: diameter 20 μm, thickness 0.1 μm) in 2 l of $H_2O$ adjusted to a pH of 2.2 at 75° C. over a period of 1 hour with stirring (1200 rpm). Stirring is continued for 15 minutes, and the pH is brought to 4.0. 250 ml of aqueous $FeCl_3$ solution (containing 4.7 g of Fe; adjusted to a pH of 3–4) are then added.

The reaction product is filtered off with suction, washed, dried at 120° C., screened (mesh size 100 μm), then calcined at 800° C. for 30 minutes and screened again (mesh size 65 μm).

The material obtained by the above process and having a metal oxide content of 25% is a golden-colored pigment suitable in particular for cosmetic applications.

EXAMPLE 7: Coating of boron nitride with carmine

In a stirred reactor, the following two aqueous solutions:

a) 10 g of carmine dissolved in 150 ml of $H_2O$ (brought to a pH of 11.0 with NaOH)

b) 5 g of $AlCl_3 \times 6 H_2O$ dissolved in 150 ml of $H_2O$ are simultaneously added to a suspension of 50 g of BN (particle size: diameter 20 μm, thickness 0.1 μm) in 2 l of $H_2O$ adjusted to a pH of 5.5 at 75° C. (pH 7.0) with stirring (1200 rpm).

The reaction product is filtered off with suction washed with 8 l of $H_2O$, dried at 80° C., comminuted by means of a Culatti mill and screened (mesh size 63 μm).

The red pigment prepared in this manner has pleasant tactile properties.

EXAMPLE 8: Coating of boron nitride with chromium oxide

In a stirred reactor, a suspension to 50 g of BN (particle size: diameter 20 μm, thickness 0.1 μm) in 2 l of $H_2O$ are heated to 75° C. (pH 7.0) with stirring (1200 rpm). The pH is then brought to 6.0 with HCl (5 g/l) 600 ml of an aqueous solution containing 100 g of $KCr(SO_4)_2 \times 12 H_2O$ are then added over a period of 5 hours; during this addition the pH is maintained at 6.0 by addition of ammonia solution (125 g/l). After addition of the chromium salt solution, stirring is continued for 15 minutes.

The reaction product is filtered off with suction, washed with 10 l of $H_2O$, dried at 120° C., then calcined at 800° C. for 30 minutes and screened (mesh size 63 μm).

The product is a green pigment having a chromium oxide content of 23%, a rich hue, a silky matte luster and pleasant tactile properties.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. A pigment comprising a platelet-shaped substrate which is a metal nitride, having coated on the surface thereof at least one dye, at least one metal oxide or a mixture thereof.

2. A pigment according to claim 1, wherein the metal nitride is boron nitride or aluminum nitride.

3. A pigment according to claim 1, wherein the dye is an inorganic dye.

4. A pigment according to claim 1, wherein the dye is an organic dye.

5. A pigment according to claim 3, wherein the dye is Prussian blue.

6. A pigment according to claim 4, wherein the dye is carmine or 1,4-diketopyrrolo- (3,4-c)pyrrole.

7. A pigment according to claim 1, wherein the substrate is coated with at least one metal oxide, which is $Fe_2O_3$, $Fe_3O_4$, $Al_2O_3$, $ZrO_2$, $Cr_2O_3$, $Fe_2TiO_5$ or $TiO_2$.

8. In a cosmetic preparation comprising a pigment, the improvement wherein the pigment is one of claim 1.

9. In a cosmetic preparation comprising a pigment, the improvement wherein the pigment is one of claim 2.

10. A pigment according to claim 1, prepared by a process comprising precipitating at least one metal oxide onto the surface of the platelet-shaped substrate.

11. A pigment according to claim 1, prepared by a process comprising converting a dye precursor into a dye in the presence of a suspension of the substrate, whereby the dye is coated onto the substrate.

12. A pigment according to claim 1, prepared by a process comprising coating the substrate with a precursor of the metal oxide or dye, and converting the precursor to metal oxide or dye after said coating.

13. A pigment according to claim 1, wherein the substrate is coated with the metal oxide, and the metal oxide is a colored metal oxide.

* * * * *